(12) United States Patent
Hickling (10) Patent No.: US 7,058,184 B1
(45) Date of Patent: Jun. 6, 2006

(54) ACOUSTIC MEASUREMENT METHOD AND APPARATUS

(76) Inventor: Robert Hickling, 8306 Huntington Rd., Huntington Woods, MI (US) 48070

( * ) Notice: Subject to any disclaimer, the term of this patent is extended or adjusted under 35 U.S.C. 154(b) by 301 days.

(21) Appl. No.: 10/396,541

(22) Filed: Mar. 25, 2003

(51) Int. Cl.
*H04R 3/00* (2006.01)

(52) U.S. Cl. .......................................... 381/92; 73/646

(58) Field of Classification Search ................. 381/92; 367/13; 73/646, 641
See application file for complete search history.

(56) References Cited

U.S. PATENT DOCUMENTS

| 4,236,040 A | | 11/1980 | Chung |
| 4,532,807 A | * | 8/1985 | Tomita et al. ................. 73/602 |
| 4,620,445 A | * | 11/1986 | McKendree et al. .......... 73/647 |

FOREIGN PATENT DOCUMENTS

JP        5-288598        11/1993

OTHER PUBLICATIONS

ANSI, 1996, "Instruments for Measurement of Sound Intensity", American National Standard S1.9-1966.
P. Rasmussen, 1989, "Source Location Using Vector Intensity Measurements", S&V Magazine 23, pp. 28-33.
G. Rasmussen, 1985, "Measurement of Vector Fields", pp. 52-58, 2nd International Congress on Acoustic Intensity.
Sekiguchi et al., 1992, Applied Acoustics, 37, pp. 305-323.
Suzuki et al., 1995, Journal Acoustic Society of Japan, (E), 16, 4, pp. 232-238.
Hickling et al., 2000, Journal Acoustic Society of America, 97(2), pp. 856-866.

* cited by examiner

*Primary Examiner*—Brian T. Pendleton
(74) *Attorney, Agent, or Firm*—Reising Ethington Barnes Kisselle P.C.

(57) ABSTRACT

Method and apparatus for simultaneous acoustic measurement at a point (M) in space of the three components of the sound intensity vector. A preferred omnidirectional vector probe (40) includes a central ring (42) with four small, microphones on tubes attached to the ring spaced from one another in a regular tetrahedral arrangement. The tubes are parallel to the axis of the ring, two on one side (58) and two on the reverse side (60) of the ring, with two of the microphones pointing in one direction and two in the opposite direction. The microphone signals are processed by an analog-to-digital converter feeding a digital signal processor (68) and employing a cross-spectral formulation to compute a sound intensity vector at the measurement point (M). Sound velocity and pressure can also be determined at this point. The resulting data may be outputted on a computer screen or other device (70). Additional related features and methods are disclosed.

11 Claims, 6 Drawing Sheets

ACOUSTIC MEASUREMENT METHOD AND APPARATUS

TECHNICAL FIELD

This invention relates to the measurement of the sound-intensity vector and, more particularly, to methods and means of performing such measurement with four small microphones.

BACKGROUND OF THE INVENTION

Previous Attempts to Measure the Sound-Intensity Vector

The sound-intensity vector, or sound power flow per unit area, is defined as the product of sound pressure and sound velocity. It is difficult to measure as a function of time and is usually determined as a function of frequency. Ways of measuring sound intensity are described in 1. F. J. Fahy, 1995, "Sound Intensity", Second Edition, E& FN Spon, An imprint of Chapman and Hall, London.
2. Anon., 1996, "Instruments for Measurement of Sound Intensity", Standard ANSI S1.9-1996, American National Standards Inst.

Sound intensity is not measured directly. It involves the use of a measurement calculation. Generally only one component of the intensity vector is measured using a pair of microphones. Two-microphone instruments are discussed almost exclusively by Fahy and in the ANSI standard, except that on pages 112 and 113 of Fahy two instruments are described that measure all three components of the intensity vector using four or more microphones.

The first of these instruments uses a probe consisting of three pairs of condenser microphones aligned face-to-face along three Cartesian axes. A probe of this type is manufactured, for example, by GRAS Sound & Vibration ApS in Denmark, as model number 50VI, and is described in 3. P. Rasmussen, 1989, "Source Location using Vector Intensity Measurements", Sound and Vibration Magazine, Vol. 23, pages 28–33.

Each pair of microphones is phase matched to provide better accuracy at low frequencies. Six microphones are used because it is easier to select phase matched condenser microphones in pairs, during manufacture. However six is more than is necessary, making the probe particularly unwieldy. A requirement for accuracy in the measurement calculation is that the sensitivity of the probe is omnidirectional; i.e. is equally sensitive to sound from all directions. However, because the six microphones have manufacturing variability and do not respond identically, the sensitivity of the GRAS probe is not omnidirectional. The usual calibration in the field at a single frequency cannot correct for this. Also the structure of the six-microphone probe prevents it from making measurements close to a source. Two sizes (typically 12 and 50 mm) of solid spacers are used to separate the faces of the three pairs of microphones in the probe. The smaller spacer is used for accuracy at higher frequencies and the larger for accuracy at lower frequencies. This means that the probe can not make accurate measurements at the same measurement point, concurrently at both low and high frequencies. Although it would be possible to output data on sound pressure and velocity with this instrument, no attempt was made to do this. Also azimuth-elevation plots were not used by P. Rasmussen to represent the direction of a sound source.

The second instrument for measuring the three components of sound intensity cited by Fahy was manufactured by Ono Sokki in Japan as model MI-6420. It uses a probe consisting of four condenser microphones positioned at the vertices of an imaginary regular tetrahedron. The tetrahedral arrangement is well known. Originally it appears to have been mentioned by 4. G. Rasmussen, 1985, "Measurement of Vector Fields", pages 52–58, Proc. Second International Congress on Acoustic Intensity, CETIM, Senlis, France.

and discussed later by

5. L. M. C. Santos, C. C. Rodrigues and J. L. Bento-Coelho, 1989, "Measuring the Three Dimensional Acoustic Intensity Vector with a Four-Microphone Probe", Proceedings of INTER-NOISE 89, 965–968.

A regular tetrahedron has the basic geometric property that lines joining the midpoints of opposite edges form a set of Cartesian axes, thus providing a ready-made coordinate system for determining the components of the sound intensity vector, with the measurement point at the origin. This property is used by the Rasmussens and by Santos et al, but surprisingly it was not used in the Ono-Sokki instrument. Instead one of the coordinate axes is assumed to pass through a microphone that protrudes ahead of the other three, as described by 6. H. Suzuki, "Three dimensional acoustic intensity measuring device", Japanese Patent No. 0528898, Nov. 2, 1993.

This coordinate system appears to have been used first by

7. K. Segiguchi, S. Kimura and T. Hanyuu, 1992, "Analysis of Sound Field on Spatial Information using a Four-Channel Microphone System on Regular Tetrahedron Peak Point Method", Applied Acoustics, 37, 305–323.

In this latter paper the direction of a sound source is determined using time of flight, rather than from the direction of the sound-intensity vector. An account of the measurement calculation for the Ono-Sokki instrument is given in 8. H. Suzuki, S. Oguro, M. Anzi and T. Ono, 1995, "Performance evaluation of a three dimensional intensity probe", Journal. of the Acoustical Society of Japan, (E), 16, 4, pages 232–238.

Because of the singular nature of the coordinate system, the calculation is complicated and subject to error. Even though the Suzuki probe uses fewer microphones than the GRAS probe it is still somewhat unwieldy and cannot detect sound well from the direction of the microphone preamplifiers and leads. As with the GRAS instrument, the microphones in the probe do not respond identically, so that the sensitivity of the probe is not omnidirectional. Also the instrument cannot make accurate measurements concurrently at both low and high frequencies. No attempt is made to present data on sound pressure and sound velocity. Also the Ono-Sokki and the Segiguchi instruments do not use practical azimuth-elevation plots to indicate the direction of a sound source.

Condenser and Electret Microphones

The GRAS, Ono-Sokki and Segiguchi instruments all use condenser microphones. A condenser microphone is generally made with a stainless steel membrane and other metal parts. It is very stable, making it suitable for use as a standard. However, it requires a pre-amplifier, usually contained in a metal tube, which has to be included as part of the structure of the probe Condenser microphones are relatively large. The microphones in the GRAS and Ono-Sokki systems are about 12.7 and 7 mm in diameter. The center of sensitivity of a microphone can not be assumed to be the geometric center of the membrane. Hence, for larger microphones, it is not possible to make an accurate determination of the inter-microphone spacing in the probe. This spacing has to be known accurately for best accuracy in the measurement calculation. As shown later, the problem of locating the center of sensitivity of a microphone is greatly alleviated with small microphones that use a thin film of polarized material called an electret Measurement Calculation Sound intensity is generally determined using the cross-spectral formulation, first derived in 1977 (see Fahy) for a two-microphone probe. This formulation relates sound intensity to the cross spectrum of the sound pressures at the microphones. It was discussed by 9. J. Y. Chung, "Sound Intensity Meter", U.S. Pat. No. 4,236,040, Nov. 25, 1980.

The formulation uses finite-difference approximations based on the requirement that the microphone spacing is less than the wavelength of the sound being measured. This requirement places an upper limit on the frequency range of the measurement. A three-dimensional version of the cross-spectral formulation was used by 10. R. Hickling and W. Wei, 2000, "Use of pitch-azimuth plots in determining the direction of a noise source in water with a vector sound-intensity probe", Journ. Acoust. Soc Amer, 97(2), pp 856–866.

In this paper the probe consists of four hydrophones in the tetrahedral arrangement. Since the hydrophones do not have the same frequency response, the sensitivity of the probe is not omnidirectional. Also the hydrophone spacing is not known precisely so that the measurement calculation is correspondingly less accurate and the measurement point is not known precisely. Hickling et al employ azimuth-elevation plots to represent the direction of a sound source. Other types of representation are used by P. Rasmussen and by Segiguchi et al.

BACKGROUND OF THE INVENTION—OBJECTS AND ADVANTAGES

The recent availability of small, sensitive electret microphones has made possible a practical and precise apparatus and procedure for measuring the three components of the sound intensity vector. The probe uses four microphones in the tetrahedral arrangement. The instrument can be used by technicians with normal computer skills and requires no in-depth acoustical training. What is needed and desired is:

(a) a probe that is easily handled
(b) a probe where the inter-microphone spacing is known accurately
(c) a means of normalizing and calibrating the microphones to make the probe omnidirectional
(d) a probe where the position of the measurement point is known accurately.
(e) a means of measuring sound intensity at a single point over a broad frequency range.
(f) a probe that is inexpensive
(g) mathematically efficient methods of measurement calculation that can be readily incorporated into a digital signal processor.
(h) a system where the direction of a sound source is represented in a practical and useful manner.
(i) a system that provides ancillary sound-velocity and sound-pressure data in addition to sound-intensity data.

Further objects and advantages of this invention will become apparent from a consideration of the following description and drawings.

SUMMARY OF THE INVENTION

The present invention includes and utilizes an instrument and method, which simultaneously measures the three components of the sound-intensity vector. The instrument includes a probe with omnidirectional sensitivity (to be explained), consisting of four small microphones positioned at the vertices of an imaginary regular tetrahedron. The probe is linked to a digital signal processor that calculates the three components of the sound-intensity vector, using the cross-spectral formulation (to be described later) based on finite-difference approximations (to be explained), and presents the results on a computer monitor or other output device.

A major factor in the invention is the recent availability of small electret microphones, which provides much greater flexibility in design of the structure of the probe and facilitates many of the improvements described here. Instead of a preamplifier, these microphones have a very small JFET (Junction Field Effect Transistor) within the microphone. Examples of small electret microphones are the FG series from Knowles Electronics LLC, of Ithaca Ill., which have a diameter of about 2.6 mm, and the EM series of Primo Microphones Inc., of McKinney, Tex., which have a diameter of about 5.8 mm. Because of their small size the center of sensitivity and inter-microphone spacing of electret microphones can be determined more precisely. This makes the measurement calculation more accurate. The Knowles FG series microphones have a sensitivity comparable to much larger condenser microphones, which makes them particularly suited to this invention. An important additional factor is that electret microphones are much cheaper than condenser microphones. Also the leads are much narrower. Their only drawback appears to be that they are less stable. However this can be compensated for by the normalization and calibration procedure described here. Small microphones can be positioned more closely, permitting measurements to be made at higher frequencies.

In the probe, use is made of the geometric property of a regular tetrahedron where the lines joining the mid-points of opposite edges pass through a central point, forming a set of Cartesian axes. Measurements are made at the origin, i.e. the geometric center of the tetrahedron The axes determine the direction of the vector components of sound intensity.

A feature of the invention is that the probe includes a small compact support structure for the microphones, that may have a ring of diameter d with four microphones in tubes attached to the ring, two tubes pointing in one direction parallel to the axis of the ring and two pointing in the opposite direction on the reverse side of the ring. Each pair of microphones lies in a plane on diametrically opposite sides of a circumference, the pair on one side being rotated ninety degrees relative to the pair on the other side, one pair being a distance $d/\sqrt{2}$ from the other. The center of the ring is the measurement point. The distance d is such that it is smaller than the shortest wavelength of sound being measured.

Measurement accuracy is ensured by a novel normalization and calibration procedure to make the sensitivity of the probe omnidirectional by making the frequency responses of the four microphones appear identical in the signal processor. The procedure also makes the signals from the microphones in the probe more accurate.

Also, in accordance with another aspect of the invention, it is possible to perform accurate measurements over a broader frequency range than before, with a nested set of two or more tetrahedral arrangements with different spacing d, having the same orientation and measurement point.

Yet another feature is that the sound-intensity vector provides a compact and accurate way of determining the direction of a sound source in air. This can be displayed on a monitor screen in the form of an easily understood elevation-azimuth plot or other suitable representation. Elevation-azimuth plots were used by Hickling et al. Other representations were used by Segiguchi et al and by P. Rasmussen. The practicality of the elevation-azimuth representation can be demonstrated by a suitable holder for the sound-intensity probe. With this holder the elevation and azimuth of the probe can be adjusted either by hand or by remote digital control, so that it points at a sound source. Direction can then be indicated by laser pointers attached to the holder. Finding the direction to a noise source at a known location is the only way of checking the accuracy of the sound-intensity vector.

Another feature of the holder is that the narrow leads from the four microphones are routed so as to reduce interference with the sound field, thus helping to preserve the ommidirectional nature of the probe. This can be accomplished, by laying a lead along a radial spoke of the holder and thence around the outer frame to the handle and the digital signal processor. The handle of the holder can contain batteries for the laser pointers.

Yet another feature is that the measurement system provides ancillary data on the other two basic quantities of acoustics, namely sound velocity and sound pressure.

Although there are a number of facets to this invention, it has a single purpose, namely to provide a practical, accurate and inexpensive instrument and method for measuring the sound-intensity vector.

These and other features and advantages of the invention will be more fully understood from the following description of certain specific embodiments of the invention taken together with the accompanying drawings.

DESCRIPTION OF THE PREFERRED EMBODIMENT

Figures 1, 2, 3:
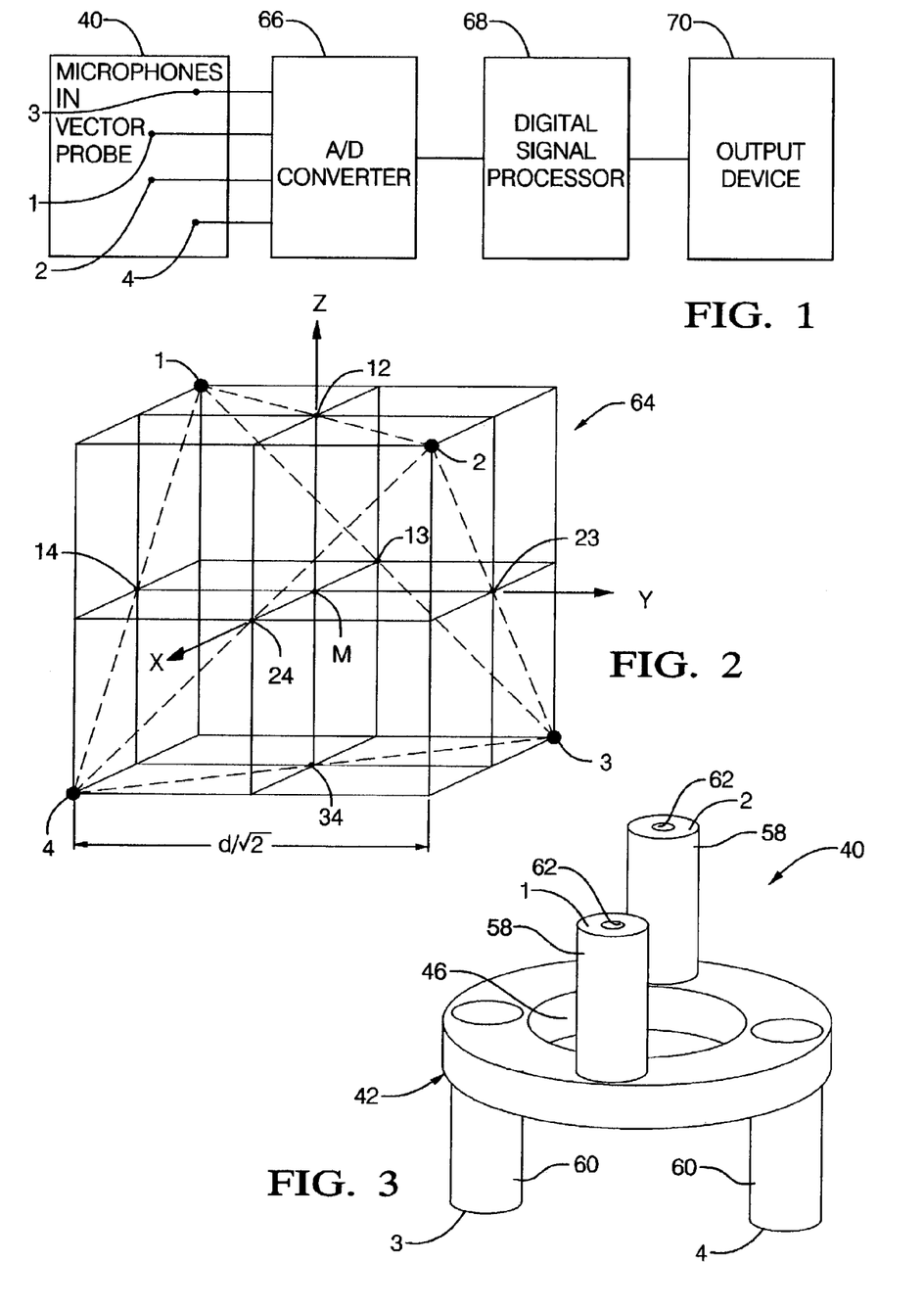
FIG. 1 is a block schematic diagram illustrating the vector probe, digital signal processor and other apparatus utilized in carrying out the method of the present invention.
FIG. 2 is a cubic lattice diagram showing the geometry of the tetrahedral arrangement of microphones and the relation of the microphones to a system of Cartesian coordinates with the origin M where measurements are made.
FIG. 3 is a perspective view of an acoustic vector probe forming a part of the invention.
Figure 8:
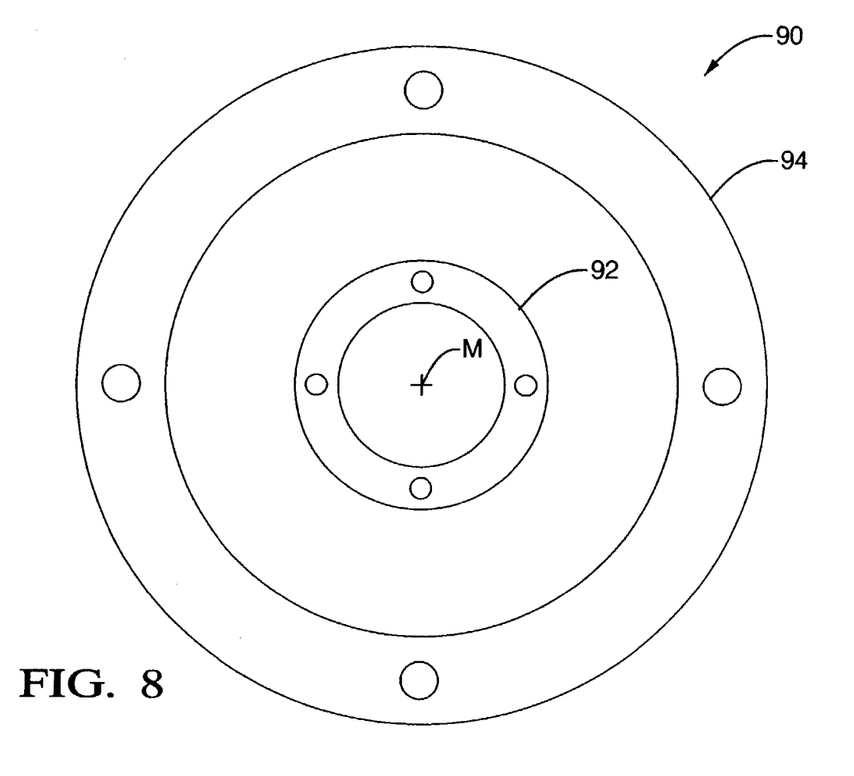
FIG. 8 is a plan view of a nested pair of vector probes with the same orientation and measurement point for extending the frequency range of the measurement.
Figure 9:
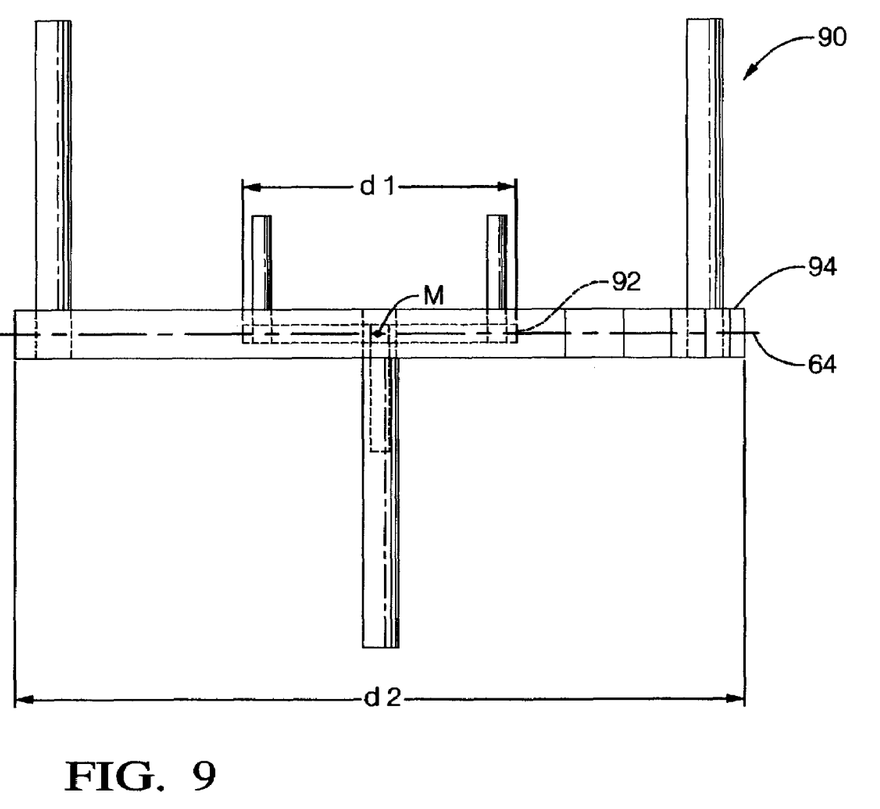
FIG. 9 is a side view of a nested pair of vector probes with the same orientation and measurement point.

FIG. 1 is a block diagram illustrating the acoustic measurement apparatus of the present invention. Block 40 represents the vector probe 40 carrying microphones 1, 2, 3 and 4. The four microphones are connected to a converter 66 that converts the analog signals from the microphones to digital form for input to a digital signal processor 68. The processor normalizes the digitized signals using transfer functions determined using a novel technique to be described later. At the measurement point, it computes the three components of the sound-intensity vector and, additionally, the three components of the sound-velocity vector and the sound pressure, using mathematical relations to be subsequently discussed, and presents the results on a monitor screen or other output device indicated by numeral 70. The invention uses a cross-spectral formulation, to be subsequently described, to determine sound intensity. The signal processor can also determine the direction of a sound source from the components of the sound intensity vector by a method to be described, presenting the results on the monitor screen or other device 70. The signal processor could have eight or more input channels corresponding to two or more nested acoustic vector probes, as shown in FIGS. 8 and 9. For the first time in such an application, the invention uses very small electret microphones. The vector probe 40 is compact and inexpensive. It can be used in applications such as noise control and architectural acoustics.

In FIG. 2, the geometric placement of the microphones in the tetrahedral arrangement is shown inserted within a cubic lattice 64 having 6 faces with midpoints 12, 13, 14, 23, 24, 34. Microphones 1 through 4 are located at the vertices of an imaginary regular tetrahedron. Lines through the midpoints of the opposite faces of the lattice pass through an origin M, which is the measurement point, and form X, Y and Z axes of the cubic lattice 64. The lines between the microphones form diagonals (not shown) across the faces of the cubic lattice, which also represent the edges of the regular tetrahedron and pass through the midpoints 12, 13, 14, 23, 24 and 34 with a length of dimension d. These lines form hypotenuse lines for the respective faces of the cubic lattice 64 so that the edges of the sides of the lattice have dimension d/$\sqrt{2}$.

Figure 4:
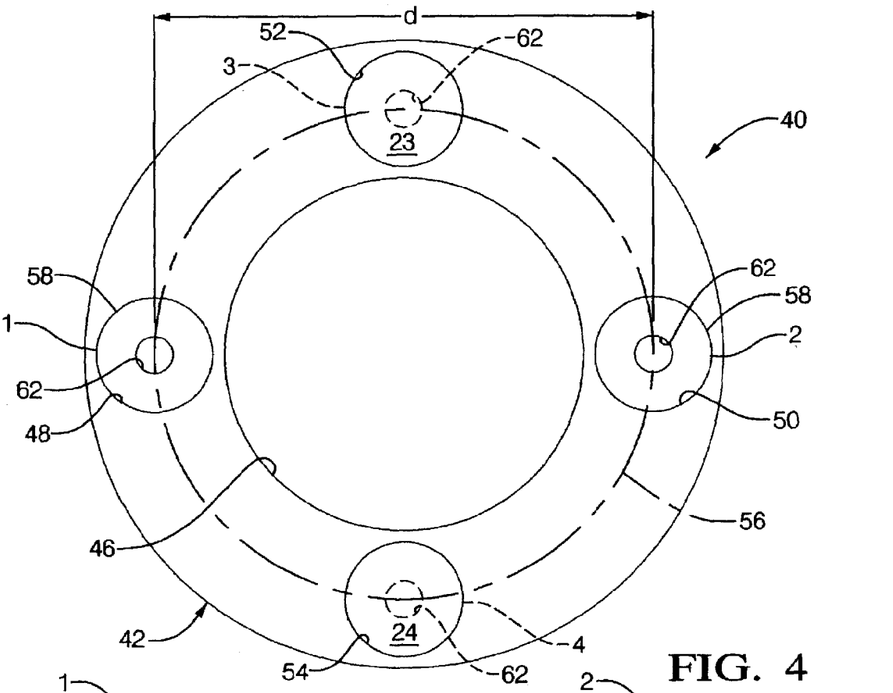
FIG. 4 is a side view of the probe of FIG. 3.
Figure 5:
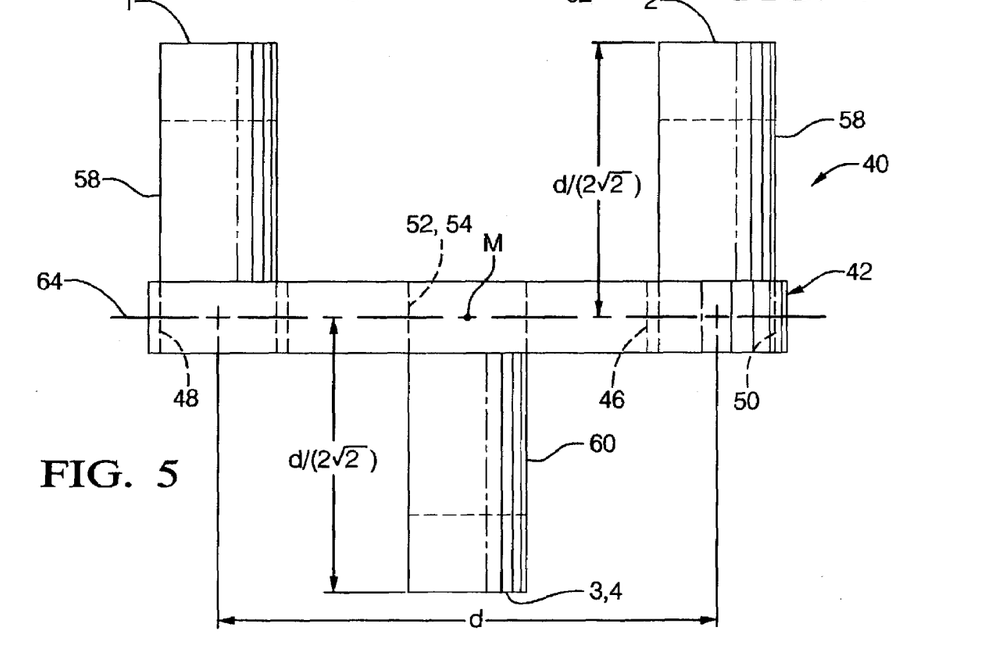
FIG. 5 is a plan view of the probe in FIG. 3

In FIGS. 3, 4 and 5, numeral 40 generally indicates an acoustic vector probe formed in accordance with the invention. Probe 40 includes a fixture 42 being an annular member formed as a ring with a central opening 46. Protruding from the ring are four support tubes for the microphones parallel to the axis of the ring, two on one side of the ring pointing in one direction and two on the reverse side pointing in the opposite direction. These tubes are spaced around the ring at ninety degree intervals at openings in the ring at 48, 50, 52 and 54, and centered on an annular centerline 56 having a diameter d. The pair of tubes 58 on one side of the ring is attached to the ring coincident with diametrically opposite openings 48 and 50, and the pair of tubes 60 on the reverse side of the ring is attached to the ring coincident with diametrically opposite openings 52 and 54. The outer ends of the support tubes 58, 60 are each a distance $d/(2\sqrt{2})$ from the central base plane 64 of the ring and a distance $d/\sqrt{2}$ from each other. Within the ends of the two support tubes 58 are located microphones 1, 2 and within the ends of the support tubes 60 are located microphones 3 and 4.

The four microphones are substantially identical and include sound admitting orifices 62 which are located with their upper surfaces flush with the ends of the tubes 58 in the case of the microphones 1, 2 and flush with the ends of tubes 60 in the case of microphones 3, 4. The microphones are preferably small electret microphones such as the FG series available from Knowles Electronics LLC, of Ithaca Ill., or the EM series of Primo Microphones Inc., of McKinney, Tex. The Knowles microphones are very small having outer diameters of less than 2.6 mm with similar body lengths, while the Primo EM microphones typically have an outside diameter of about 5.8 mm. Despite their small size the Knowles FG microphones have a sensitivity comparable to larger microphones. The smallness of these microphones makes it possible to locate their centers of sensitivity more precisely and hence to determine the separation distance d more exactly.

For the finite difference approximations in the measurement calculations to be valid, the microphone spacing d has to be smaller than the shortest wavelength (corresponding to the highest frequency f) being measured, satisfying the condition $kd/2<1$, where $kc=2\pi f$, k being the wave number, c the speed of sound in air (about 344 m/s) and f the upper frequency limit. For example, if the instrument is designed for an upper frequency limit of 5 kHz, which is typical of most machinery noise, the corresponding wave number k is about 0.0913. Hence d has to less than about 20 mm. Suppose d is 15 mm. The two microphones then protrude from the central base plane of the ring a distance $d/(2\sqrt{2})$, which is about 5.30 mm.

It is seen from FIGS. 3, 4 and 5 that the Knowles FG series electret microphones readily fit into this configuration, as do other microphones such as the Primo EM series. Because of the smallness of the preferred Knowles microphones, it is possible to make the separation distance d much less than 15 mm, thus permitting measurements to be made at frequencies up to about 15 kHz. For larger microphones, particularly of the condenser type, it would not be possible to attain this high a frequency. In principle, of course, there is no reason that condenser microphones could not be used. The structure for holding the microphones could be different from that in FIGS. 3, 4 and 5, provided the locations of the microphones continues to correspond to those shown in FIG. 2. The advantages of the structure in FIGS. 3, 4 and 5 are: (a) the microphones are symmetric on the two sides of the base ring so that they detect sound equally from both directions; (b) the measurement point M is well defined; (c) the procedure for normalizing and calibrating can be applied easily. Since the dimensions of the probe are required to be much less than the wavelengths being measured, the effect of diffraction will be insignificant.

Figure 6:
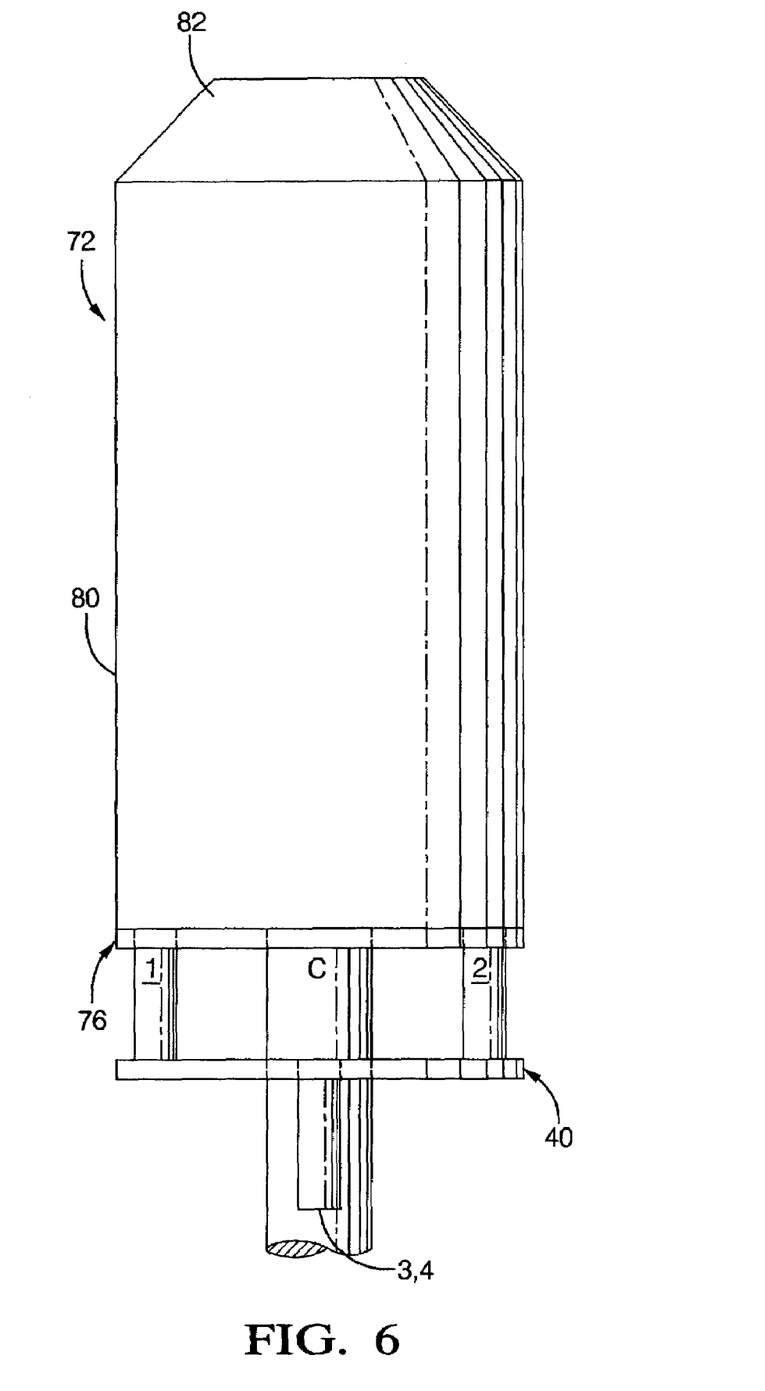
FIG. 6 is a side view of a calibration apparatus for normalizing and calibrating the microphones in the vector probe.
Figure 7:
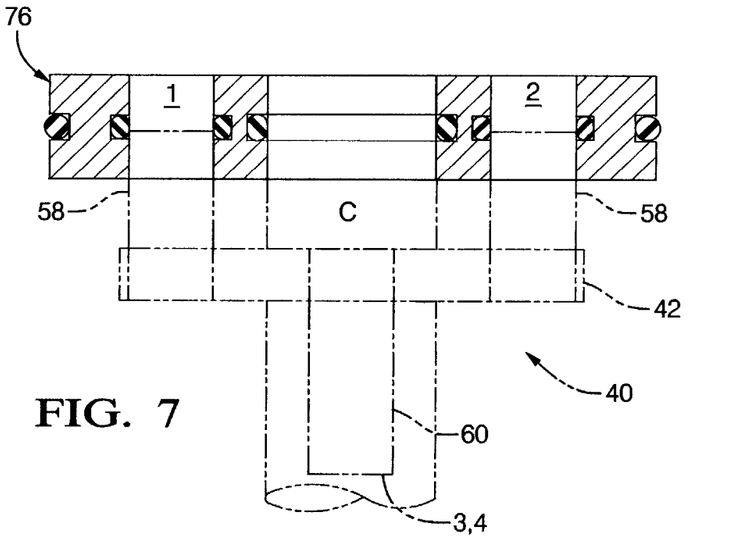
FIG. 7 is a side view of a fixture applied to the vector probe for use with the calibration apparatus, and positioned for assembly into the calibration apparatus, for normalizing and calibrating the two pairs of microphones, one pair on each side of the ring of the vector probe.

FIGS. 6 and 7 depict an apparatus for normalizing and calibrating the vector probe whose use will be explained in the next section.

FIGS. 8 and 9 illustrate how the frequency range of the measurements can be extended by using a pair of nested vector probes with the same orientation and measurement point. As will be explained later the smaller inner probe extends the accuracy of the measurements to higher frequencies and the larger outer probe to lower frequencies. The two sets of measurements are performed simultaneously and are merged in the signal processor to cover the combined frequency range.

Figure 10:
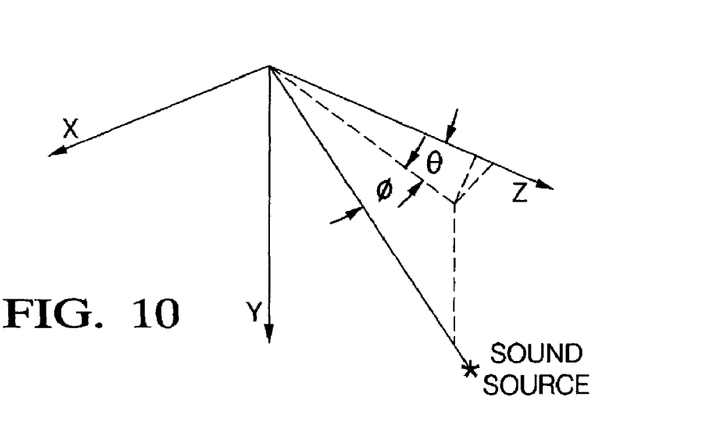
FIG. 10 shows the coordinate system for determining the direction of a sound-intensity vector in azimuth and elevation, relative to the orientation of a vector probe.

FIG. 10 shows how the X, Y, Z components of the sound-intensity vector are expressed in terms of azimuth and elevation to indicate the direction of a sound source. This is discussed more fully later.

Figure 11:
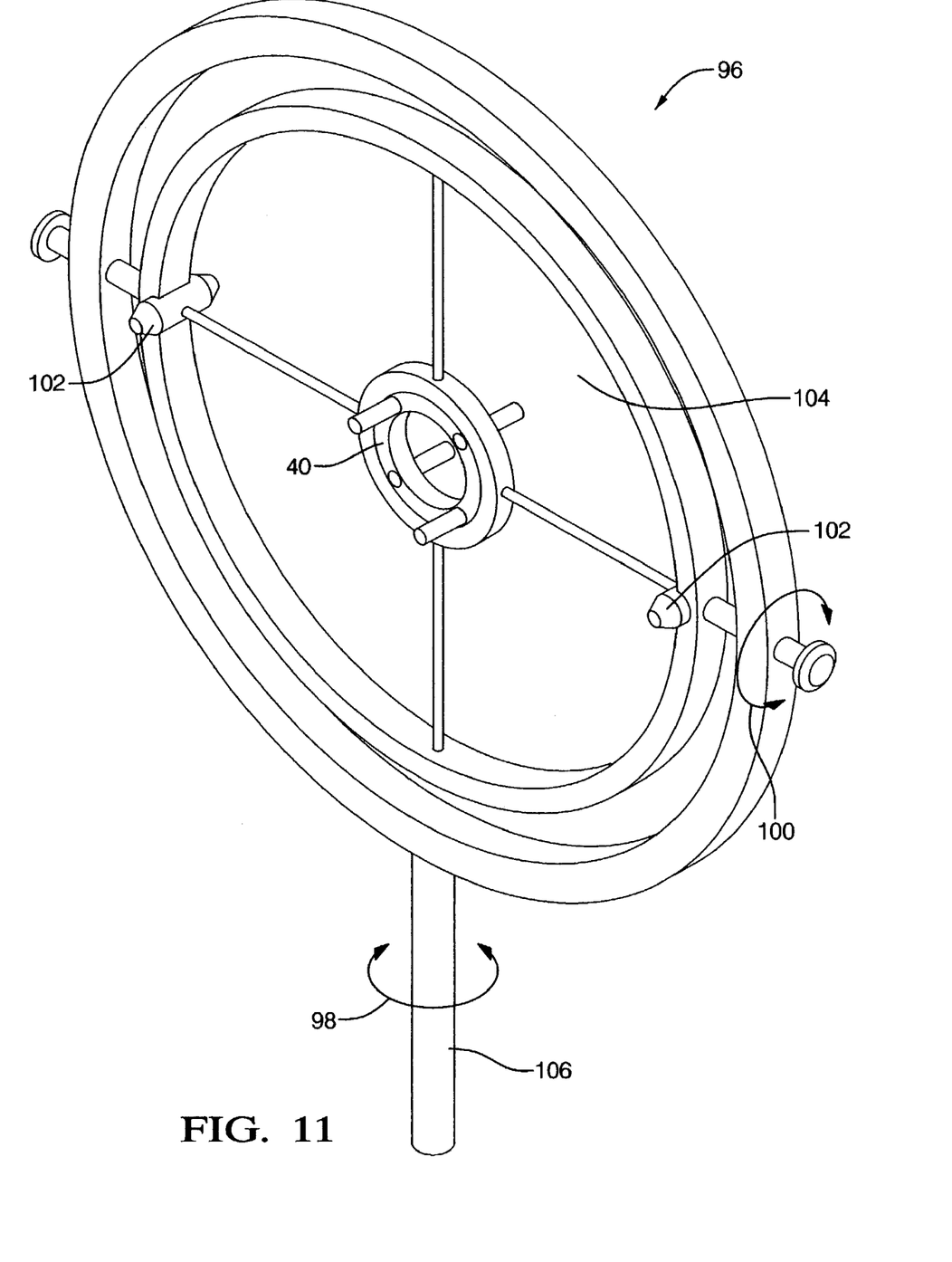
FIG. 11 shows a holder for a vector probe that can be adjusted in azimuth and elevation, with spokes spreading radially from each microphone, the direction of a sound source being indicated by small laser pointers in the holder.

FIG. 11 shows a holder for the vector probe that can be adjusted in azimuth and elevation. The direction of a noise source is indicated by laser pointers. The narrow leads (not shown) from each microphone are routed along the spokes of the holder and around the holder's outer frame to the handle, proceeding then to the analog-to-digital converter and the digital signal processor. The handle can contain batteries for the laser pointers in the holder.

Normalization and Calibration of the Microphones in the Probe

To measure acoustic intensity accurately, the acoustic sensitivity of the array of four microphones in the probe has to be omnidirectional, i.e. equally sensitive to sound from any direction. Because of their small size relative to the acoustic wavelength, the sensitivities of the electret microphones in the probe are individually omnidirectional. However, if the sensitivity of the tetrahedral arrangement in the probe is to be omnidirectional, the constituent microphones have to respond identically. In the normalization procedure described here, the microphones are made to respond identically in the digital signal processor by determining the transfer function between each microphone and a standard calibration microphone. The procedure also calibrates the microphones. This procedure is designed for use with the probe in the field.

Presently microphones are calibrated in the field with a hand-held calibrator only at a single frequency. More complete calibration has to be performed at a special laboratory away from the test site, using procedures that are considered beyond the capabilities of a typical test engineer. Such procedures are described, for example, in 11. V. Nedzelnitsky, 1997, "Calibration of Pressure and Pressure Gradient Microphones.", Vol. 4, Chap. 157, Encyclopedia of Acoustics, edited by M. J. Crocker, John Wiley & Sons, Inc., New York.

In the invention, normalization and calibration of the vector probe is performed with the closed-chamber apparatus 72, shown in FIG. 6. A condenser microphone C, such as the Bruel & Kjaer quarter-inch model 4136 or eighth-inch model 4138, is used as a standard comparison microphone for normalization and calibration of the microphones in the probe. The procedure is performed using the fixture 76 shown in FIG. 7, inserted into one end of the calibration tube 80, with the loudspeaker 82 at the other end, emitting pseudo-random white noise or other broadband time-invariant or stationary signals.

The fixture 76 in FIG. 7 places the standard microphone C in the same plane as microphones 1 and 2 of the probe supported by the two tubes 58. Signals received simultaneously at the microphone 1 and the calibration microphone C, denoted respectively by p1(t) and pC(t) in the time domain, are recorded by the signal processor 38 and transformed into the frequency domain using discrete Fourier transforms (DFTs) indicated by the italic prefix F. DFT techniques are described in texts such as, 12. W. H. Press, S. A. Tuekolsky, W. T. Vetterling and B. P. Flannery, 1996, "Numerical Recipes In C++: The Art of Scientific Computing", Cambridge University Press, Cambridge, UK.

The complete normalization and calibration procedure can be best described as follows. Standard DFT techniques are performed to determine the transfer function H1C(f) between microphone 1 and the calibration microphone C, as follows $$H1C(f)=G1C(f)/G11(f) \quad (1)$$

where G1C(f) is the cross-spectrum between the signal at microphone 1 and the calibration microphone C, given by $$G1C(f)=FpC(f).Fp1(f)^* \quad (2)$$

and G11(f) is the auto-spectrum of the signal at microphone 1 given by $$G11(f)=Fp1(f).Fp1(f)^* \quad (3)$$

where the asterisks denote the complex conjugate. To make the signal Fp1(f) at microphone 1 look like the signal FpC(f) at the calibration microphone C, it is multiplied by the transfer function in Equation (1) to give $$Fp1C(f)=Fp1(f).H1C(f) \quad (4)$$

The process is repeated for microphone 2 using relations corresponding to Equations (1) through (4), specifically $$H2C(f)=G2C(f)/G22(f) \quad (5)$$

where $$G2C(f)=FpC(f).Fp2(f) \quad (6)$$

and $$G22(f)=Fp2(f).Fp2(f) \quad (7)$$

To make Fp2(f) look like FpC(f), Fp2(f) is multiplied by the transfer function in Equation (5) to give $$Fp2C(f)=Fp2(f).H2C(f) \quad (8)$$

Transfer functions for microphones 3 and 4 are obtained in the same way by reversing the vector probe so that the tubes 60 are inserted into the fixture 76 placing microphones 3 and 4 in the same plane as the calibration microphone C. In this way all four microphones in the probe can be made to look like the calibration microphone C, making the sensitivity of the probe omnidirectional and also calibrating the individual microphones. The transfer functions are stored in the signal processor for later use in measurements with the probe.

Different types and sizes of the fixture 76 can be used for different sizes of probes, particularly for the nested probes shown in FIGS. 8 and 9 and for the probe holder in FIG. 11.

Measurement Calculation

Calculations to determine the components of the sound-intensity vector at a point in space, from measurements at the four microphones in the vector probe, are performed in the signal processor. The calculations also determine the other two basic quantities of acoustics, namely sound velocity and sound pressure, at the same measurement point. The calculation method is best described as follows.

At the microphones 1, 2, 3 and 4 at the vertices of the regular tetrahedron in FIG. 2, the corresponding sound pressures p1, p2, p3 and p4 are measured and digitized. To ensure omnidirectionality and accuracy the discrete Fourier transforms (DFTs) of the sound pressures are then computed, normalized and calibrated using the transfer-function procedure described in the previous section, giving the modified transforms Fp1(f), Fp2(f), Fp3(f) and Fp4(f). For simplicity, the frequency dependence (f) will be dropped. Finite difference approximations (derived from Taylor series expansions) are then applied to obtain the DFTs of the sound pressures at the six midpoints of the edges of the regular tetrahedron at 12, 13, 14, 23, 24 and 34 in FIG. 2, giving respectively $$Fp12 = (Fp1 + Fp2)/2 \quad (9)$$

$$Fp13 = (Fp1 + Fp3)/2$$

$$Fp14 = (Fp1 + Fp4)/2$$

$$Fp23 = (Fp2 + Fp3)/2$$

$$Fp24 = (Fp2 + Fp4)/2$$

$$Fp34 = (Fp3 + Fp4)/2.$$

These approximations are accurate to the second order, i.e. order $(kd)^2/4$, provided.

$$kd/2<1 \quad (10)$$

The components of the sound-intensity vector at the measurement point M are determined from the sound pressure DFTs in Equation (9), using the cross-spectral formulation described by Fahy, Chung and Hickling et al. The components are $$FIX=-Im\ CS[Fp24,\ Fp13]/(\rho 2\pi f(d/\sqrt{2}))$$

$$FIY=-Im\ CS[Fp23,\ Fp14]/(\rho 2\pi f(d/\sqrt{2}))$$

$$FIZ=-Im\ CS[Fp12,\ Fp34]/(\rho 2\pi f(d/\sqrt{2})) \quad (11)$$

where Im is the imaginary part and CS is the cross spectrum of the sound pressures at the midpoints of the opposite edges of the imaginary regular tetrahedron in FIG. 2, and p is the density of the fluid medium, which is approximately 1.2 kg/m$^3$ for air. The amplitude is given by $$FIA=\sqrt{[FIX^2+FIY^2+FIZ^2]} \quad (12)$$

Sound intensity is expressed in SI units of watts per meter squared per second.

The classical far field approximation for sound intensity is still widely used and may be employed in the computation as a comparison. This approximation is valid for plane and spherical waves and gives the sound-intensity amplitude as $$FTAff=|FpM|^2/(\rho c) \quad (13)$$

where c is the speed of sound in the fluid medium (approximately 344 m/s for air) and FpM is the finite-difference approximation of the DFT of the sound pressure at the measurement point M given by $$FpM=(Fp1+Fp2+Fp3+Fp4)/4 \quad (14)$$

in SI units of pascals per hertz.

The components of the sound-velocity vector are obtained from the finite-difference approximations of the X, Y and Z components of the pressure gradient at the measurement point M, which are $$FDpX=(Fp24-Fp13)/(d/\sqrt{2})$$

$$FDpY=(Fp23-Fp14)/(d/\sqrt{2})$$

$$FDpZ=(Fp12-Fp34)/(d/\sqrt{2}) \quad (15)$$

where again these are accurate to second order. The X, Y and Z components of the DFTs of the sound-velocity vector are then $$FVX = K\ FDpX$$
$$FVY = K\ FDpY$$
$$FVZ = K\ FDpZ \quad (16)$$

where the coefficient $K=i/(p2\pi f)$, i being the square root of −1. In SI units these components are in meters per second per hertz. The amplitude of each component is given by $$FVXA=|FVX|,\ FVYA=|FVY|\ \text{and}\ FVZA=|FVZ|.$$

The amplitude of the sound velocity vector is then given by $$FVA=\sqrt{(FVXA^2+FVYA^2+FVZA^2)} \quad (17)$$

Unlike the sound-intensity vector, the sound-velocity vector has a 180 degree ambiguity in direction.

The above equations can be developed using software such as LABVIEW and MATLAB and converted into C++ or other suitable computer language for use in the signal processor.

Extending the Frequency Range of the Measurements by Combining two or more Tetrahedral Arrangements of Microphones The vector probe has two limitations in the frequency range, one at high frequencies and the other at low frequencies. At high frequencies it is necessary to satisfy the condition in Equation (10) to preserve the accuracy of the finite difference approximations. Hence, to extend the frequency range as high as possible, the spacing d between the microphones must be as small as possible. However if the microphones are too close, error is introduced at low frequencies due to taking the difference between almost equal quantities, as in Equation (15). This error can be reduced only by increasing the microphone spacing d. Clearly it is not possible both to increase and decrease the spacing d for measurements at the same point. To extend the frequency range at both high and low frequencies, it is necessary to have at least two tetrahedral arrangements, one for the upper end of the frequency scale and the other for the lower end.

FIGS. 8 and 9 show a nested set 90 of two acoustic probes 92, 94 arranged for this purpose. The probes are similar to those shown in FIGS. 3 and 4 but differ in size, specifically in the dimension d, to cover the upper and lower parts of the frequency range. The probes 92, 94 are nested one inside the other with the same orientation and measurement point M, and measurements are made simultaneously at both probes. To cover a desired frequency range, it may be necessary to have more than two probes in the nested set. Correspondingly the number of input channels to the digital signal processor has to be increased to equal the number of microphones in the nested set. Also calculation in the digital signal processor ensures that measurements in different parts of the frequency range merge appropriately with each other.

Using the Vector Probe to Determine the Direction of a Sound Source in Air

The acoustic vector probe determines the three components of the sound intensity vector at the measurement point M internal to the probe. This information can then be used to find the direction of a sound source, assuming that sound propagates in a straight line from the source to the measurement point. The direction of a sound source can be determined in terms of the horizontal (azimuth) angle θ.and the vertical (elevation) angle φ. The combination of these two angles specifies the direction of the source, as shown in FIG. 10. Other angles could be used, but azimuth and elevation are commonly used and easily understood. The vector probe can point horizontally in the direction of the Z-axis while the Y-axis is vertical as shown in FIG. 2. The angles θ and φ are determined from the relations $$\theta=\arccos(FIZ/FIXZ) \quad (18)$$

and $$\phi=\arcsin(FIY/FIA) \quad (19)$$

where $FIXZ=\sqrt{[FIX^2+FIZ^2]}$ and the other terms come from Equations (15) and (16). The angles θ and φ are functions of frequency. They can be represented over the frequency range by a set of discrete points in an elevation-azimuth (or vertical-horizontal) plot on a monitor screen, relative to the direction of the probe, as in Hickling et al. In free space the points will generally coincide. Tests in an anechoic chamber can then be used to check the omnidirectionality and accuracy of the probe. However in practice there will be a scatter of the points due to the acoustic environment. Color-coding of the points on the monitor screen can show the frequency dependence of the scatter. Color-coding is a new idea that was not used by Hickling et al, but it can be a rich source of information. The components of the velocity vector can be used to determine direction in a similar way, except that there is a 180-degree ambiguity in the data.

The assumption that sound propagates in a straight line from the source to the probe is not always valid, because conditions such as temperature and turbulence in the acoustical medium may affect the transmission path. Corrections can be made. However, we will restrict ourselves to the straight-line assumption. In addition to being used in architectural acoustics and noise control, the direction-finding capabilities of a vector probe could provide a model for the directional hearing of animals.

An example of a device for determining direction is shown in FIG. 11. Here a vector probe 40 is shown contained in a holder 96 which can be adjusted in azimuth 98 and elevation 100. The device can be hand-held and includes laser pointers 102 to show the direction of a noise source. A human operator can adjust the holder in the direction indicated by the processor. The laser pointers then point to the source. It would be possible also to locate the holder remotely and to operate it with a computer controller. The fixture shown in FIG. 7 can be adapted so that the probe can be normalized and calibrated without having to be removed from the holder.

FIG. 11 indicates that the leads from the microphones can be routed along the spokes 104 and around the outer frame of the holder to the signal processor. It also indicates that the laser pointers can be powered by batteries in the handle 106 of the holder.

While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims.

The invention claimed is:

1. Acoustic measurement apparatus comprising:
   an omnidirectional acoustic vector probe including four small microphones supported by a space frame at the vertices of an imaginary regular tetrahedron;

a first pair of said microphones facing a same first direction a second pair of said microphones in a backward-facing relationship with said first pair and facing a same opposite direction;

said microphones connected to an analog digital converter for conversion of analog signals to digital form;

said converter connected to a digital signal processor programmed to normalize and calibrate the signals and to compute sound intensity, velocity and pressure at a measurement point in space; and said processor connected to an output apparatus for outputting the measurement results of the computations.

2. The invention as in claim 1 wherein the processor is additionally programmed to compute the direction of a sound source from the direction of the sound-intensity vector.

3. The invention as in claim 2 wherein the direction of a sound source is displayed on a computer screen as a plot in a grid relative to a coordinate system of the vector probe.

4. The invention as in claim 3 wherein frequency dependence of points plotted in the grid on the computer screen is illustrated by color-coding.

5. The invention as in claim 1 where said microphones have maximum dimensions less than 6 mm.

6. The invention as in claim 1 including at least one input channel for each of the microphones in the acoustic measurement apparatus.

7. A precisely constructed acoustic vector probe comprising:

a space frame supporting four substantially identical microphones, at the vertices of an imaginary regular tetrahedron, each microphone spaced the same distance d from the other microphones, a first pair of the microphones facing a same first direction and lying in a plane separated by a distance $d/\sqrt{2}$ from a parallel plane containing a second pair of the microphones, in a back-to-back relationship with said first pair and facing a same opposite direction from said first direction and defining a set of Cartesian axes formed by lines joining the midpoints of opposite edges of the tetrahedron whose center is the measurement point of the probe, the space frame including a supporting member lying midway between the said planes and having spaced openings with microphone support means extending from the openings.

8. A precisely constructed acoustic vector probe comprising:

a space frame supporting four substantially identical microphones, at the vertices of an imaginary regular tetrahedron, each microphone spaced the same distance d from the other microphones, two of the microphones lying in a plane separated by a distance $d/\sqrt{2}$ from a parallel plane containing the other two microphones and defining a set of Cartesian axes formed by lines joining the midpoints of opposite edges of the tetrahedron whose center is the measurement point of the probe, the space frame including a supporting member lying midway between the said planes and having spaced openings with microphone support means extending from the openings; and wherein said support means includes tubes extending normal to said member and supporting said pairs of microphones, one pair lying on one side of said member facing in one direction and the other pair on the reverse side facing in the opposite direction.

9. The invention as in claim 8 wherein said member is a ring having one pair of said microphones and said tubes spaced from the other said pair of microphones, alternating equally on a diameter of dimension d, said tubes extending normal to a mid base plane of the ring a distance $d/(\sqrt{2})$, the center of said mid base plane being the measurement point of the probe.

10. A precisely constructed acoustic vector probe comprising:

a space frame supporting four substantially identical microphones, at the vertices of an imaginary regular tetrahedron, each microphone spaced the same distance d from the other microphones, two of the microphones lying in a plane separated by a distance $d/\sqrt{2}$ from a parallel plane containing the other two microphones and defining a set of Cartesian axes formed by lines joining the midpoints of opposite edges of the tetrahedron whose center is the measurement point of the probe, the space frame including a supporting member lying midway between the said planes and having spaced openings with microphone support means extending from the openings; and where the vector probe is contained in a holder which can be adjusted so that the probe points in the direction of a sound source and the direction of the source can be indicated by laser pointers or other means.

11. The invention as in claim 10 where the said holder can be adjusted by hand or controlled by a digital controller.

* * * * *

UNITED STATES PATENT AND TRADEMARK OFFICE
CERTIFICATE OF CORRECTION

| | | |
|---|---|---|
| PATENT NO. | : 7,058,184 B1 | |
| APPLICATION NO. | : 10/396541 | |
| DATED | : June 6, 2006 | |
| INVENTOR(S) | : Robert Hickling | |

It is certified that error appears in the above-identified patent and that said Letters Patent is hereby corrected as shown below:

IN THE SPECIFICATION

Col. 7, Line 28, After "where" delete "kc=2nf" insert -- $kc=2\pi f$ --
Col. 10, Line 44, After "squared" delete "per second"
Col. 10, Line 58, After "units of pascals" delete "per hertz"
Col. 11, Line 12, Before "The amplitude" delete "per hertz"

Signed and Sealed this

Second Day of October, 2007

JON W. DUDAS
*Director of the United States Patent and Trademark Office*